United States Patent [19]

Atkinson et al.

[11] Patent Number: 5,079,431
[45] Date of Patent: Jan. 7, 1992

[54] ELECTRON BEAM SCENARIO SIMULATOR AND METHOD OF TESTING A SENSOR

[75] Inventors: John H. Atkinson, Laguna Beach; Robert L. Caswell, Fullerton, both of Calif.

[73] Assignee: The United States of America as represented by the Secretary of the Army, Washington, D.C.

[21] Appl. No.: 600,895

[22] Filed: Oct. 22, 1990

[51] Int. Cl.⁵ .............................................. H01J 1/46
[52] U.S. Cl. .............................. 250/443.1; 250/494.1; 250/495.1
[58] Field of Search ............... 250/493.1, 494.1, 495.1, 250/252.14; 273/348.1

[56] References Cited
U.S. PATENT DOCUMENTS

| | | | |
|---|---|---|---|
| 4,572,958 | 2/1986 | Durand et al. | 250/495.1 |
| 4,999,502 | 3/1991 | Midavaine | 250/493.1 |
| 5,012,112 | 4/1991 | Flint et al. | 250/493.1 |

Primary Examiner—Jack I. Berman
Assistant Examiner—Kiet T. Nguyen
Attorney, Agent, or Firm—Freddie M. Bush; Robert L. Broad

[57] ABSTRACT

A simulator and method of testing a sensor wherein an electron gun mounted in a vacuum chamber directs a stream of electronic onto a target plate made up of a heat sink backing sheet and a heat insulating coating sheet adhered to the backing layer to form small hot spots on the coating sheet. The target plate may be a sheet of copper to which is adhered a coating layer of glass or a sheet of aluminum to which is adhered a coating layer of aluminum oxide. Infrared radiation from the hot spots is collimated and passed through an optical system which forms an image of the hot spots on the sensor to be tested.

8 Claims, 2 Drawing Sheets

ELECTRON BEAM SCENARIO SIMULATOR AND METHOD OF TESTING A SENSOR

DEDICATORY CLAUSE

The invention described herein may be manufactured, used and licensed by or for the Government for governmental purposes without the payment to us of any royalties thereon.

BACKGROUND OF THE INVENTION

1. Field of the Invention

This invention relates to scenario simulators and methods for testing sensors.

2. Prior Art

Sensors are used to detect ballistic missiles, decoys and other objects moving through the atmosphere. Generally, an optical system of some type is used to project an image of a section of sky to be monitored onto a sensor which is sensitive to infrared radiation. Objects in this section of sky will thus be detected, with the location of the image of the object on the sensor being indicative of the direction in which the object is located.

In order to be assured that a given sensor is in good working order prior to being put into use, it would be desirable to test the sensor before it is put into operation. So far as known, there is no satisfactory method of forming an image having the desired spatial distribution of radiance and temperature range for accurate testing of an infrared sensor.

SUMMARY OF THE INVENTION

A scenario simulator and method for testing an infrared sensor wherein a stream of electrons is impinged on a plate made up of a heat conductive backing sheet and a heat insulating coating sheet adhered to the backing sheet, with the electrons striking the coating sheet to form small hot spots on the coating sheet. The backing sheet is a heat sink material selected from the group consisting of copper and aluminum. If a copper backing sheet is used, the coating sheet is a thin layer of glass. If the backing sheet is aluminum, the coating sheet is aluminum oxide. An image of the hot spots on the sheet is projected onto the sensor to be tested to determine whether the sensor will detect the hot spots which simulate incoming missiles. The process is carried out in a vacuum chamber and the backing sheet is cooled to a temperature below the minimum temperature to which the sensor will respond.

DETAILED DESCRIPTION OF THE INVENTION

Figure 1:
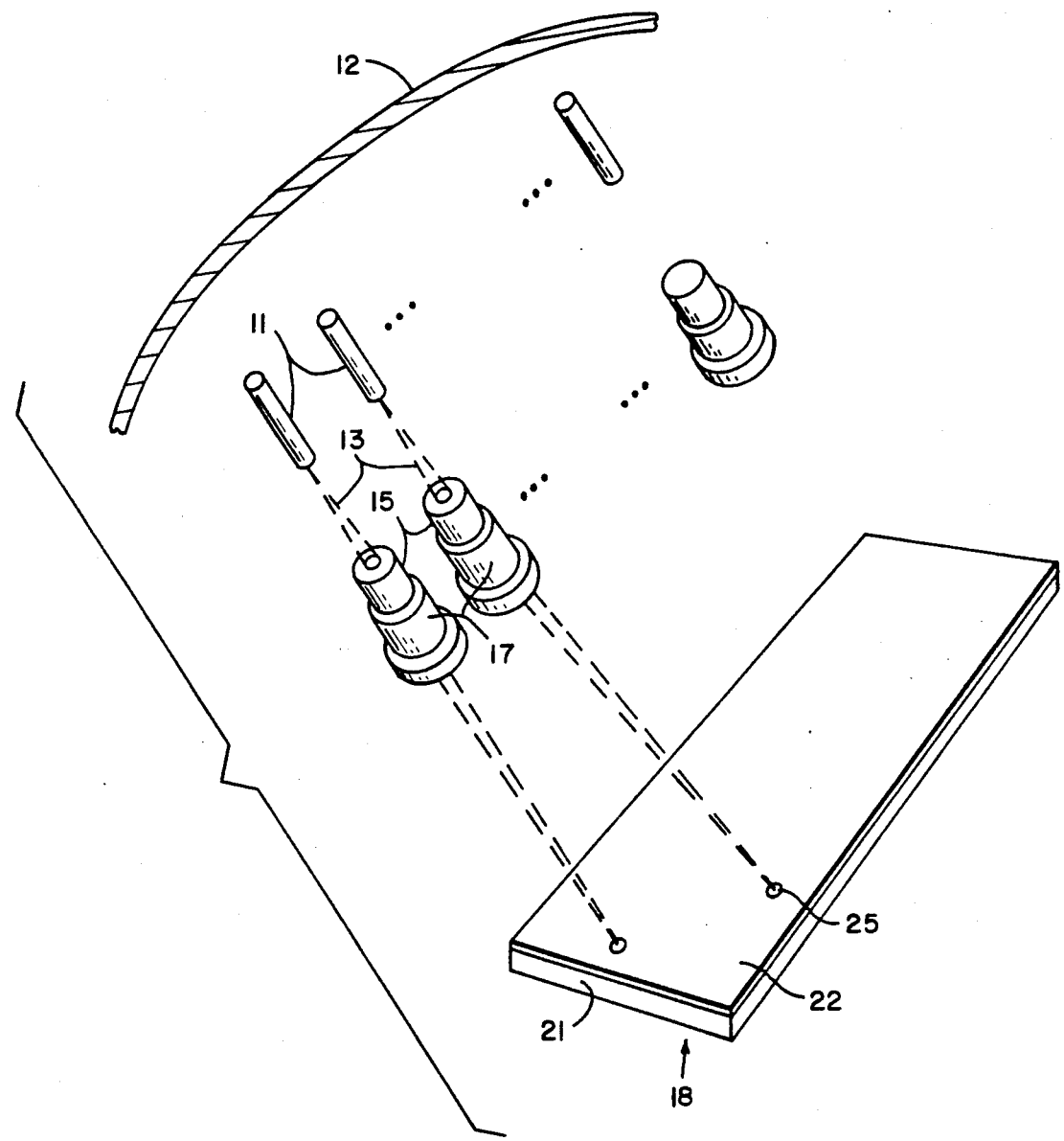
FIG. 1 is a fragmentary perspective view showing electron guns mounted in a vacuum chamber and positioned to direct streams of electrons onto the target plate of this invention.

Referring now in detail to the drawings, there is shown a plurality of electron guns 11 of a known type mounted in a vacuum chamber, with a portion of the wall of the chamber being indicated by reference numeral 12. The electron guns 11 each direct a stream of electrons 13 through a focusing coil 15 and a deflection yoke 17 in a known manner to impinge on a target plate 18.

The target plate 18 is made up of a rigid support or backing sheet 21 which acts as a conductive heat sink and a coating sheet 22 adhered to the support sheet. While the support 21 sheet acts as a conductive heat sink, the coating sheet 22 acts as a heat insulator. The target plate may be made up of a sheet of aluminum coated with a coating sheet of aluminum oxide or a support sheet of copper coated with a coating sheet of glass. The thickness of the support sheet should be great enough that the sheet is relatively rigid, with a thickness of about 1 cm generally being sufficient. The thickness of the coating sheet is preferable within the range of 1 micron to about 1 mm.

The target plate 18 is cooled in a known manner to a temperature below the minimum temperature to which the sensor will respond, i.e., the temperature at which the plate will radiate infrared radiation at an intensity sufficient to trigger the sensor. If desired, the plate 18 may be cooled to about 4 degrees Kelvin, which is the temperature of outer space. However to be operative it is only necessary to cool the plate 18 to a temperature low enough that the plate will not radiate sufficient infrared to trigger the sensor.

The electron beams 13 impinge on the coating 22 to form hot spots 25 which radiate infrared radiation at an intensity which is high enough to be detected by the sensor. The size of the hot spots 25 will depend on the size of the object. For a relatively small object at a very large distance, the hot spots will be very small. Because of the fact that these spots 25 are hotter than the remainder of the plate 18, the spots can be detected by the sensor.

Figure 2:
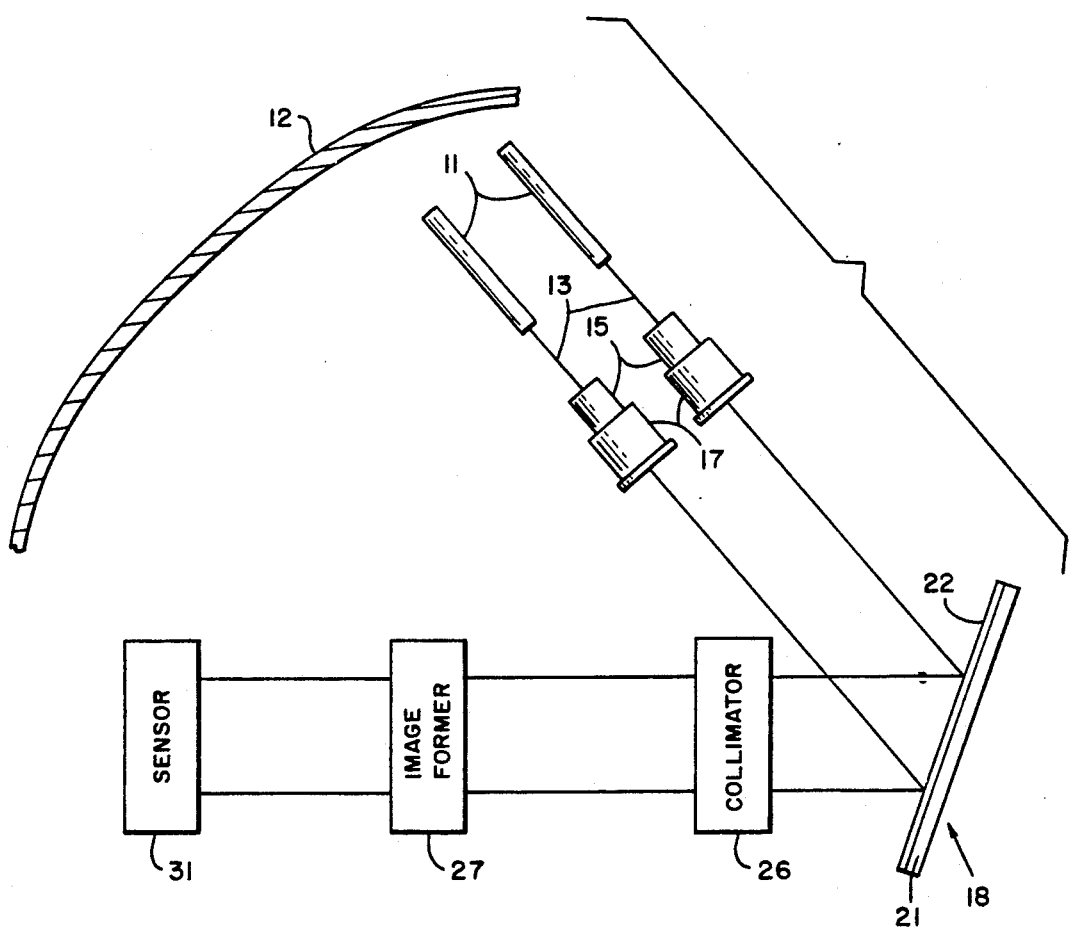
FIG. 2 is a schematic side view showing the apparatus of the invention.

Infrared radiation from the hot spots 25 is passed through an optical system (FIG. 2) made up of a collimating system 26 of a known type and an image forming system 27 of a known type to fall on a sensor 31 to be tested. The collimation of radiation from the target plate will cause the radiation at the sensor to appear to come from infinity. By using this system, it can be determined, in advance of being putting into use, whether the sensor is performing properly.

What is claimed is:

1. A system for testing a sensor which is sensitive to infrared radiation, comprising
   a. a vacuum chamber;
   b. an electron gun mounted in the chamber for projecting a stream of electrons;
   c. a target plate positioned to intercept said stream of elecrtrons, said target being a thin layer of a thermally insulating material on a thick plate of a thermally conducting material, said stream of electrons impinging on the layer to generate a hot spot on said layer;
   d. means for projecting an image of said hot spot onto a sensor to be tested.

2. The system of claim 1 wherein said thick plate has a thickness of about 1 cm and the layer has a thickness within the range of 1 micron to 1 mm.

3. The system of claim 2 wherein the projecting means is such that said image appears at the sensor to come from an infinite distance.

4. The system of claim 3 wherein said thick plate is cooled to a temperature below the minimum temperature to which the sensor will respond.

5. A process for testing a sensor sensitive to infrared radiation, comprising a. projecting a stream of electrons onto a target plate to form localized hot spots on said plate, said plate being selected from the group consisting of a backing sheet of aluminum with a coating sheet of aluminum oxide or a backing sheet of copper with a coating sheet of glass, said electrons impinging the coating sheet, and b. projecting an image of said hot spots onto the sensor to test said sensor, said process being carried out under vacuum.

6. The process of claim 5 wherein the backing sheet is cooled to a temperature below the minimum temperature to which the sensor will respond.

7. The process of claim 6 wherein a plurality of electron beams are projected onto the target plate to simulate a plurality of incoming missiles.

8. The process of claim 7 wherein infrared radiation from said hot spots is collimated prior to reaching the sensor to simulate infrared-radiating objects at an infinite distance.

* * * * *